US008459572B2

(12) United States Patent
Hering et al.

(10) Patent No.: US 8,459,572 B2
(45) Date of Patent: Jun. 11, 2013

(54) FOCUSING PARTICLE CONCENTRATOR WITH APPLICATION TO ULTRAFINE PARTICLES

(75) Inventors: Susanne Hering, Berkeley, CA (US); Gregory Lewis, Berkeley, CA (US); Steven R. Spielman, Oakland, CA (US)

(73) Assignee: Aerosol Dynamics Inc., Berkeley, CA (US)

( * ) Notice: Subject to any disclaimer, the term of this patent is extended or adjusted under 35 U.S.C. 154(b) by 85 days.

(21) Appl. No.: 12/910,705

(22) Filed: Oct. 22, 2010

(65) Prior Publication Data

US 2011/0095095 A1 Apr. 28, 2011

Related U.S. Application Data

(60) Provisional application No. 61/279,620, filed on Oct. 24, 2009.

(51) Int. Cl.
*A62C 5/02* (2006.01)
(52) U.S. Cl.
USPC ............. 239/8; 239/1; 239/405; 239/423; 239/424; 239/589; 95/228; 96/413; 73/863.21; 73/863.22
(58) Field of Classification Search
CPC .... A62C 5/02; F23D 11/10; B05B 1/00; B05B 7/10; B05B 17/00
USPC ............. 239/1, 8, 22, 405, 418, 423, 424, 239/424.5, 589; 95/228, 288; 96/413; 73/863.12, 28.04, 863.21, 863.22
See application file for complete search history.

(56) References Cited

U.S. PATENT DOCUMENTS

| | | | |
|---|---|---|---|
| 1,514,976 A * | 11/1924 | Lewis | 239/405 |
| 3,731,464 A | 5/1973 | Brumbaugh et al. | |
| 3,901,798 A | 8/1975 | Peterson | |
| 4,301,002 A | 11/1981 | Loo | |
| 4,358,302 A * | 11/1982 | Dahneke | 239/424 |
| 4,670,135 A | 6/1987 | Marple et al. | |
| 4,689,052 A | 8/1987 | Ogren et al. | |
| 4,767,524 A | 8/1988 | Yeh et al. | |
| 4,972,957 A | 11/1990 | Liu et al. | |

(Continued)

FOREIGN PATENT DOCUMENTS

WO 2009089276 A2 7/2009

OTHER PUBLICATIONS

Demokritou et al, "A High Volume Apparatus for the Condensational Growth of Ultrafine Particles for Inhalation Toxicological Studies", Nov. 2002, Aerosol Science Technololgy 36:11 , pp. 1061-1072.

(Continued)

*Primary Examiner* — Steven J Ganey
(74) *Attorney, Agent, or Firm* — Vierra Magen Marcus LLP

(57) ABSTRACT

Technology is presented for the high efficiency concentration of fine and ultrafine airborne particles into a small fraction of the sampled airflow by condensational enlargement, aerodynamic focusing and flow separation. A nozzle concentrator structure including an acceleration nozzle with a flow extraction structure may be coupled to a containment vessel. The containment vessel may include a water condensation growth tube to facilitate the concentration of ultrafine particles. The containment vessel may further include a separate carrier flow introduced at the center of the sampled flow, upstream of the acceleration nozzle of the nozzle concentrator to facilitate the separation of particle and vapor constituents.

23 Claims, 14 Drawing Sheets

U.S. PATENT DOCUMENTS

| | | | |
|---|---|---|---|
| 5,183,481 | A | 2/1993 | Felder |
| 5,425,802 | A | 6/1995 | Burton et al. |
| 5,498,271 | A | 3/1996 | Marple et al. |
| 5,533,406 | A | 7/1996 | Geise |
| 5,788,741 | A | 8/1998 | Burton et al. |
| 5,858,043 | A | 1/1999 | Geise |
| 6,010,554 | A | 1/2000 | Birmingham et al. |
| 6,062,392 | A | 5/2000 | Birmingham et al. |
| 6,120,573 | A | 9/2000 | Call et al. |
| 6,156,212 | A | 12/2000 | Rader et al. |
| 6,290,065 | B1 | 9/2001 | Kenning et al. |
| 6,544,312 | B2 | 4/2003 | Mullinger et al. |
| 6,698,592 | B2 | 3/2004 | Kenning et al. |
| 6,712,881 | B2 | 3/2004 | Hering et al. |
| 6,726,130 | B2 * | 4/2004 | Jaubertie ............... 239/589 |
| 7,178,380 | B2 | 2/2007 | Shekarriz et al. |
| 7,232,477 | B2 | 6/2007 | Rodgers |
| 7,261,007 | B2 | 8/2007 | Haglund et al. |
| 7,325,465 | B2 | 2/2008 | Solomon et al. |
| 7,704,294 | B2 | 4/2010 | Ariessohn |
| 7,875,095 | B2 | 1/2011 | Ariessohn et al. |
| 8,104,362 | B2 | 1/2012 | McFarland et al. |
| 2002/0134137 | A1 | 9/2002 | Ondov et al. |
| 2006/0171844 | A1 | 8/2006 | Sioutas et al. |
| 2008/0083274 | A1 | 4/2008 | Hering et al. |

OTHER PUBLICATIONS

De La Mora et al., "Aerodynamic Focusing of Particles in a Carrier Gas", Oct. 1988, Journal of Fluid Mechanics, 195: 1-21.

Fuerstenau et al., "Visualization of Aerodynamically Focused Subsonic Aerosol Jets", Jan. 1994, Journal of Aerosol Science, 25:165-173.

Gupta et al., "Effects of PhysicoChemical Properties of Ultrafine Particle on the Performance of an Ultrafine Particle Concentrator", Jan. 2004, Aerosol Science and Technology 38:Suppl. 2, pp. 37-45.

Ning et al., "Field Validation of the New Miniature Versatile Aerosol Concentration Enrichment System (mVACES)", Dec. 2006, Aerosol Science and Technology 40: 1098-1110.

Rao et al., "Aerodynamics Focusing of Particles in Viscous Jets", Oct. 1993, Journal of Aerosol Science 24: 879-892.

Su et al., "Real-Time Characterization of the Composition of Individual Particles Emitted From Ultrafine Particle Concentrators", Jul. 2006, Aerosol Science and Technology, 40:437-455.

International Search Report dated Feb. 1, 2011, in International Patent Application No. PCT/US2010/053939 filed Oct. 25, 2010.

Notification Concerning Transmittal of International Preliminary Report on Patentability, dated May 3, 2012, in International Patent Application No. PCT/US2010/053939 filed Oct. 25, 2010.

Sioutas et al, "Fine Particle Concentrators for Inhalation Exposures—Effect of Particle Size and Composition", Jan. 1997, J. Aerosol Sci. vol. 28, No. 6, pp. 1057-1071.

Kim et al., "Versatile Aerosol Concentration Enrichment System (VACES) for Simultaneous In Vivo and In Vitro Evaluation of Toxic Effects of Ultrafine, Fine and Coarse Ambient Particles—Part I: Development and Laboratory Characterization", Mar. 2001, Aerosol Science 32, pp. 1281-1297.

Sioutas, et al., "Development and Evaluation of a Prototype Ultrafine Particle Concentrator", Sep. 1999, J. Aerosol Sci. vol. 30, No. 8, pp. 1001-1017.

Sioutas et al., "Inertial Separation of Ultrafine Particles Using a Condensational Growth/Virtual Impaction System", Nov. 1996, Aerosol Science and Technology, 25:4, 424-436.

Sioutas et al., "Development and Evaluation of a Prototype Ambient Particle Concentrator for Inhalation Exposure Studies", Jan. 1995, Inhalation Toxicology, 7: 633-644.

Geller et al., "A New Compact Aerosol Concentrator for Use in Conjunction With Low Flow-Rate Continuous Aerosol Instrumentation", Aug. 2005, Aerosol Science 36, 1006-1022.

* cited by examiner

FIG. 8
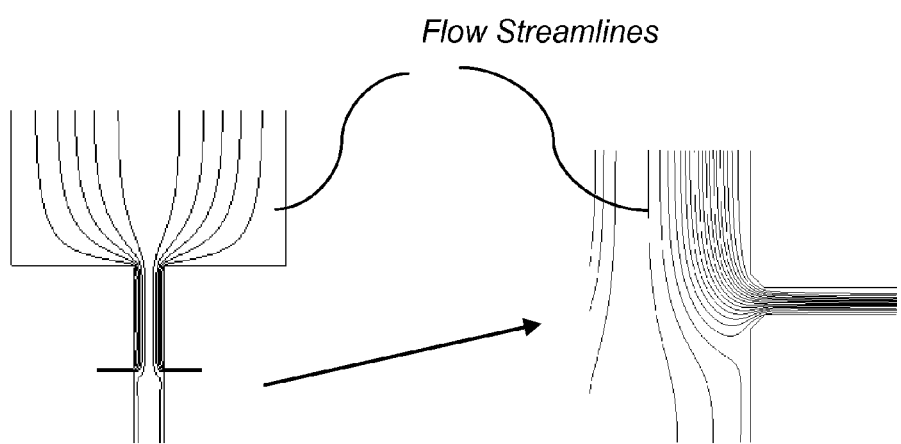
Flow Streamlines
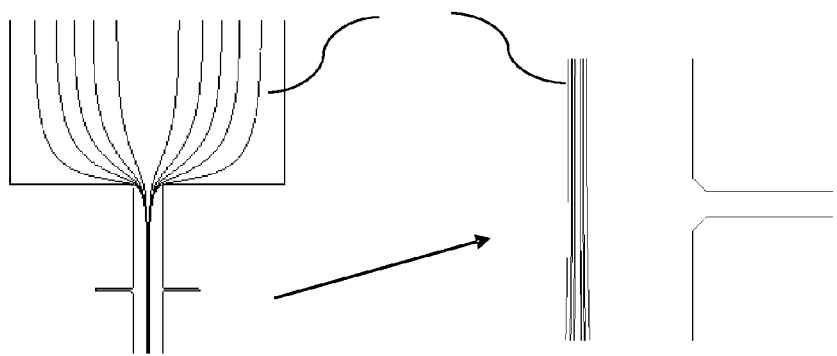
Trajectories for 3 μm particles
FIG. 9

FOCUSING PARTICLE CONCENTRATOR WITH APPLICATION TO ULTRAFINE PARTICLES

CLAIM OF PRIORITY

The present application claims priority to U.S. Provisional Application Ser. No. 61/279,620 filed Oct. 24, 2009 which is incorporated by reference herein in their entirety.

This invention was made with government support under the following Grant Nos: U.S. Dept. of Energy Grand #DE-FG02-08ER86335 and DE-FG02-04ER86179; and National Institutes of Environmental Health Grant #ES014997. The government has certain rights in the invention.

BACKGROUND

Airborne particles are ever present in the environment, and are of concern for human health, for atmospheric visibility and for climate change. Measurement of the chemical characteristics of these particles, and of the health effects associated with their inhalation is often aided by air-to-air "particle concentrators" that enrich the particle concentration in a portion of the air flow stream.

Virtual impactors are a well known type of "air-to-air" particle concentrator that use a low-velocity sampling probe to sample a particle flow exiting from a nozzle. Because of the mismatch in air velocities, those particles larger than a few micrometers are preferentially captured within the low-velocity sampling probe. This is a commonly used approach for enrichment of particles with diameters above a few micrometers, but is ineffective for the submicrometer and ultrafine particle size range of most interest for atmospheric and health-related studies.

Current "air-to-air" concentrators for small particles couple these traditional virtual impactors with condensational growth. These small particle concentrators use steam injection or warm saturators with cooling and turbulent mixing to condense water on particles present in the flow, enlarging them to supermicrometer-sized droplets prior to entering the virtual impactor. These systems are ineffective for particles below about 30 nm in diameter. Moreover, with long condensation times, these approaches have been shown to have the undesirable effect of changing the particle chemical composition.

SUMMARY

Technology is provided which uses an acceleration nozzle on a particle laden flow in a containment vessel, with the acceleration nozzle having an extraction structure and an output. The technology provides a 5- to 10-fold enhancement in the concentration of particles of a characteristic size range that are carried within an air flow or other gas. When operated in conjunction with a water condensation device, it concentrates particles over a wide size range. A particle laden sample of gas is introduced into the containment vessel including a nozzle concentrator at one end thereof. The nozzle concentrator has an acceleration nozzle and an extraction structure. Particles over a defined size range move to the centerline of the nozzle concentrator by means of aerodynamic focusing. This nozzle concentrator entrance can have a single-step, sharp edged configuration, a more gradually shaped nozzle, or a series of "steps" with multiple serial contractions. The majority, outer portion of the flow passing through the nozzle concentrator is extracted through an extraction structure in a sidewall of the nozzle concentrator, leaving the particle-laden central flow, which continues to pass through the acceleration nozzle to an output. For operation in air at atmospheric pressures, this central flow contains all of the particles that entered the nozzle concentrator and having diameters in the size range of a few micrometers. Smaller, submicrometer particles are concentrated by passing the particle laden stream through a laminar flow, water condensation growth system prior to entering the nozzle concentrator, wherein the submicrometer particles grow to a few micrometers in diameter by water condensation.

A combined condensation-nozzle concentrator system provides a 10-fold enrichment in particle concentration over a particle size range from 0.01 to 5 µm. Through incorporation of a particle free carrier air flow immediately upstream of the acceleration nozzle, this technology can be used to transfer fine and ultrafine particles from their surrounding gas into a different carrier gas flow.

BRIEF DESCRIPTION OF THE DRAWINGS

FIG. 8 shows air flow streamlines calculated numerically for a single step nozzle concentrator with 1 L/min air flow through a 0.86 mm diameter accelerating nozzle, from which 0.9 L/min of flow is extracted through a 0.1 mm slit located 5 mm downstream of the nozzle entrance.

FIG. 9 shows particle trajectories for the geometry and operating conditions of FIG. 8 calculated for unit density, spherical particles with a diameter of 3 µm diameter

DETAILED DESCRIPTION

Technology is provided which uses a nozzle concentrator structure, having an acceleration nozzle with a side flow extraction component or extraction structure, to provide a particle enriched flow to an output. In one embodiment, the present technology includes a nozzle concentrator consisting of an acceleration nozzle 104, with a flow extraction structure 103 and with an output. The nozzle concentrator may be coupled to a containment vessel which may include a water condensation growth tube to facilitate the concentration of ultrafine particles. The containment vessel may further include a separate carrier flow introduced at the center of the sampled flow, upstream of the acceleration nozzle of the nozzle concentrator to facilitate the separation of particle and vapor constituents.

Figure 1:
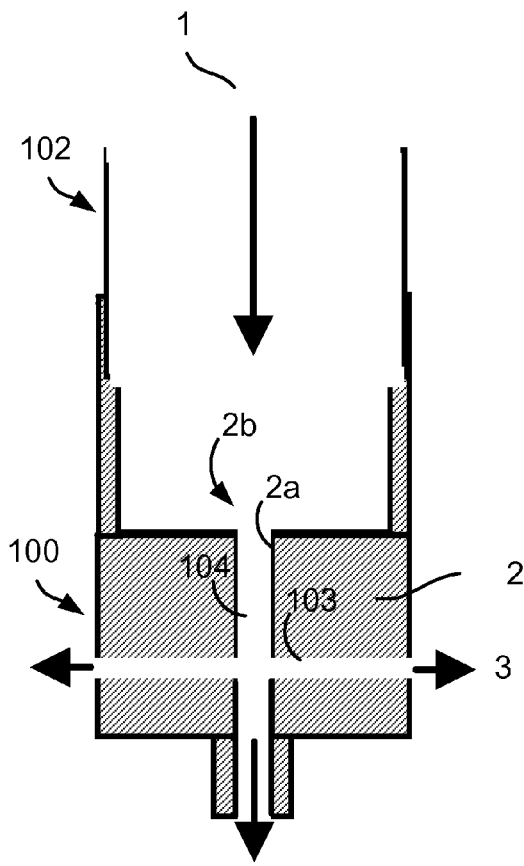
FIG. 1 illustrates the concept of the nozzle concentrator of this technology, comprised of a containment vessel and nozzle concentrator with an extraction structure.

A particle condensation apparatus using a nozzle concentrator 100 is illustrated in FIG. 1. Generally, the particle laden flow stream is introduced in a containment vessel 102 at 1, and flows through acceleration nozzle 2. In one embodiment the acceleration nozzle 2 has an interior wall 2a having a circular cross section and whose diameter or width is much smaller than the upstream dimensions of the device, such that the mean velocity of the flow increases. As the flow accelerates into the nozzle, particles of within a characteristic size range are focused near the centerline of the flow. At a few nozzle dimensions downstream of the entrance 2b of the acceleration nozzle is an extraction structure 103, illustrated in FIG. 1 as a symmetric slit or other perforation in the side wall 2a of the acceleration nozzle. A majority of the flow is extracted at 3. Under laminar conditions, the majority of this flow is the side flow; that is, flow that did not originate from near the centerline of the nozzle. The flow near the centerline, which comprises a small fraction of the total flow that entered at 1 contains the majority of the focused particles. This near centerline flow is the particle transport flow and exits the nozzle at an output 4. As described below, particles with aerodynamic diameters in the range from 1 µm to 6 µm are focused in the nozzle, and concentrated by this methodology. A flow controller, not shown, may be provided to control the flow rate of the particle laden flow in the containment vessel.

Figure 2:
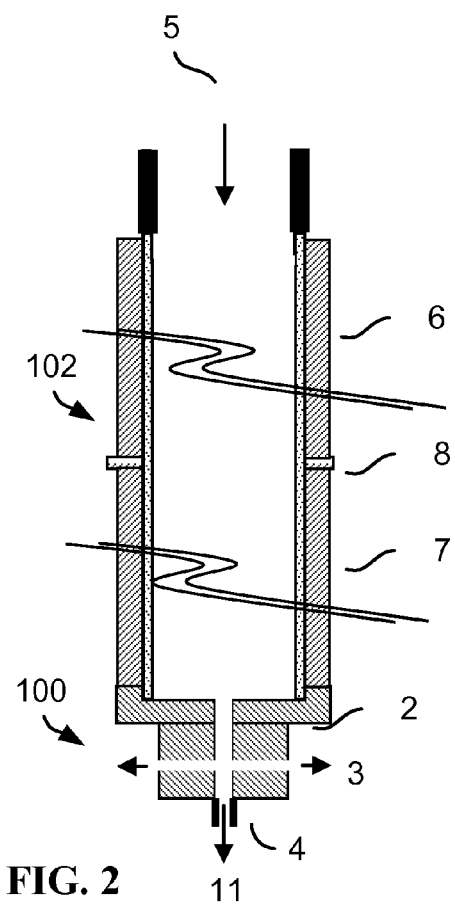
FIG. 2 illustrates the application of this nozzle concentrator to ultrafine particles by coupling with a laminar flow, water-based particle condensation system.

FIG. 2 illustrates the use of a water-based particle condensation system 105 as part of the containment vessel 102. The water based particle condensation system is positioned upstream of the nozzle concentrator to form an ultrafine particle concentrator. The particle laden sample air stream is introduced into the particle condensation system at 5. In the condensation system submicrometer and some nanometer sized particles are enlarged by water condensation to form droplets of a few micrometers. As illustrated, this is accomplished using a laminar flow, differentially diffusive water condensation system as described by U.S. Pat. No. 6,712,881, which is fully incorporated by reference herein. The flow passes through a wet-walled tube in a laminar manner. Generally, the first portion of the walls 6 are cooled, while the walls of the downstream portion 7 are warmed, separated by a thermal break 8. In the warmed portion of the wet-walled tube particles grow by water condensation because the transport of water vapor from the warmed walls is faster than the transport of sensible heat; a direct result of the higher mass diffusivity of water vapor as compared to the thermal diffusivity of air. Once enlarged, the droplets enter the nozzle concentrator 100.

Figure 3:
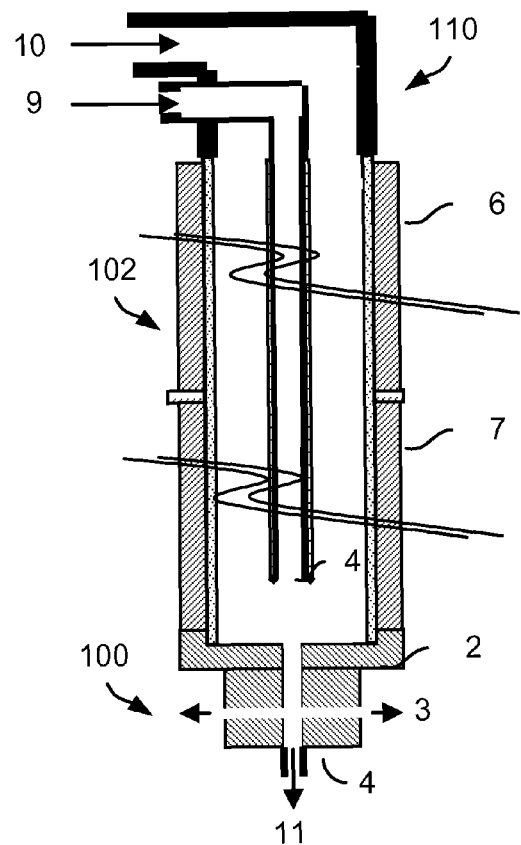
FIG. 3 illustrates application of this technology to particle-vapor separation by introduction of a clean air core flow immediately upstream of the nozzle concentrator of the ultrafine particle concentrator of FIG. 2.

FIG. 3, is a vapor-particle separator 110 used as part of the containment vessel, wherein a clean core air flow 9 is introduced immediately upstream of the acceleration nozzle of the nozzle concentrator shown in FIG. 1. The flow rate of the introduced clean air core flow is slightly higher than the flow rate of the central particle transport flow that exits at point 4. In the absence of mixing, this core flow comprises the flow near the centerline within the acceleration nozzle, and becomes the particle transport flow 11. The focused particles are essentially thrown into this core air flow as a result of their inertia. Used in conjunction with the condensation system, as shown, this provides high efficiency transfer of the particles in the sample flow 10 to a clean air flow, or other selected gas, at 11. The side flow extracted by the extraction structure 103 and exits at 3 is comprised of the sampled air, less the focused particles, plus the slight excess of clean air introduced at 9.

Figure 4:
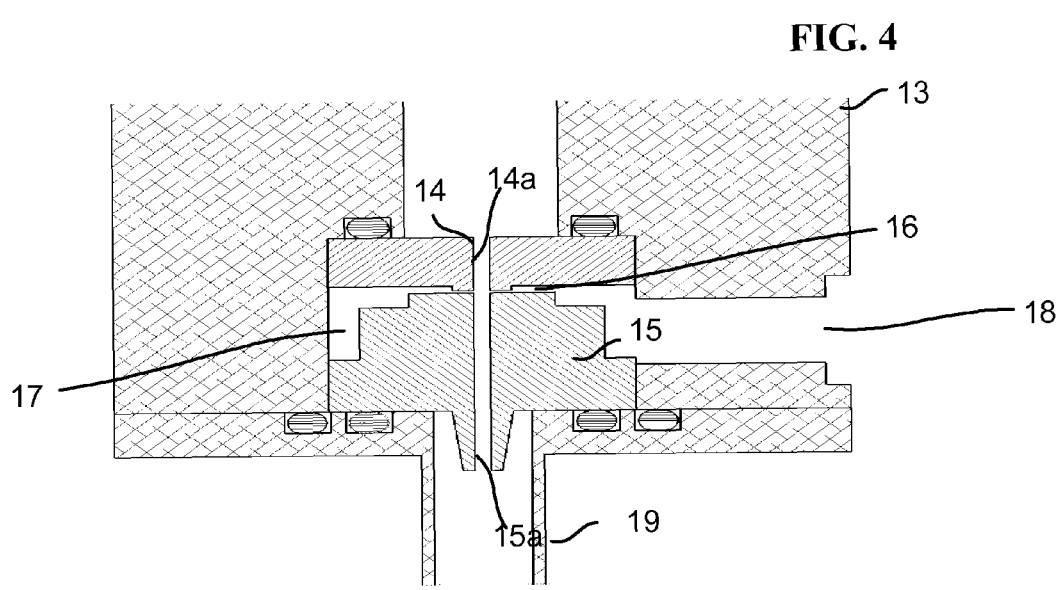
FIG. 4 shows an embodiment of the nozzle concentrator of FIG. 1.

Example embodiments of each of these aspects of the technology are shown in FIGS. 4 through 7. FIG. 4 shows a first embodiment of a nozzle concentrator 100a consisting of an approximately 8 mm diameter tube 13, an acceleration nozzle entry 14 with a nozzle interior wall 14a with an internal diameter d1 of 1 mm or less, followed by a coaxial, aligned nozzle exit piece 15 having walls 15a of the same internal diameter. These two pieces are separated by a narrow gap 16 of approximately 0.1 mm, which is smaller than the nozzle diameter, and which communicates to a cylindrically symmetric exit plenum 17 and side flow extractor tube 18. The central particle transport flow exits at 19.

Figure 5:
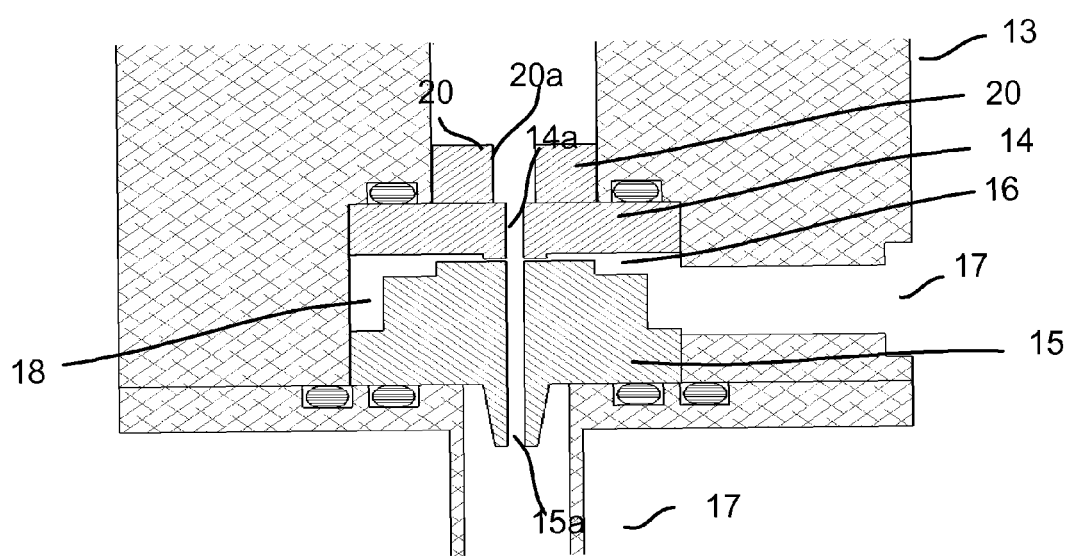
FIG. 5 shows an embodiment of the nozzle concentrator with a two-step inlet to the acceleration nozzle.

FIG. 5 shows a two-step nozzle concentrator wherein an additional orifice 20 having interior walls 20a defining a circular cross section of a somewhat larger internal diameter which is inserted upstream of the main acceleration nozzle 14.

Figure 6:
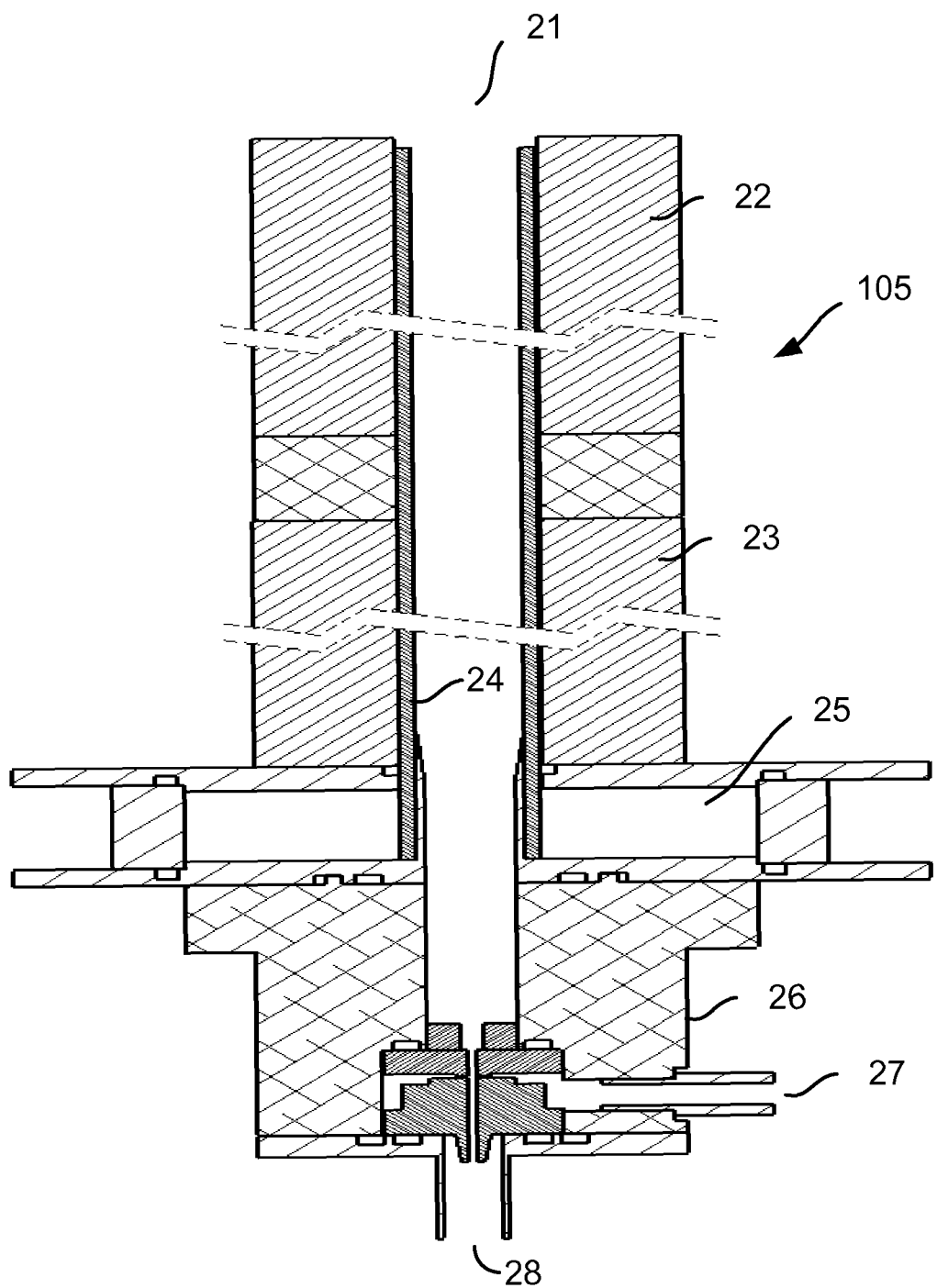
FIG. 6 shows an embodiment of the ultrafine particle concentrator of the current technology, consisting of a laminar flow, water-based particle condensation system coupled to the nozzle concentrator.

FIG. 6 shows an example embodiment of the ultrafine particle concentrator, consisting of a laminar flow condensation system 105 combined with the coupled to the nozzle concentrator illustrated in FIG. 5. A particle laden flow enters at 21, and passes through the wet-walled condensation system 105, the main components of which are the cooled preconditioner section 22, followed by the warmed growth section 23. The internal walls of 22 and 23 are lined with a hydrophilic, porous wick 24, the lower end of which sits in a water reservoir 25, and is wetted throughout by capillary action. The flow directly enters the nozzle concentrator 26. The concentrator 26 can be the double step concentrator of FIG. 5, or the single step concentrator of FIG. 4. The side flow, comprising the 70% to 95% of the sample flow, is extracted at 27. The condensationally enlarged particles are transferred to the remaining portion of the flow, referred to as the particle transport flow 28. Flow 28 can be dried, without dilution, by any number of commonly known means, to provide an ultrafine concentrated particle sample.

Figure 7:
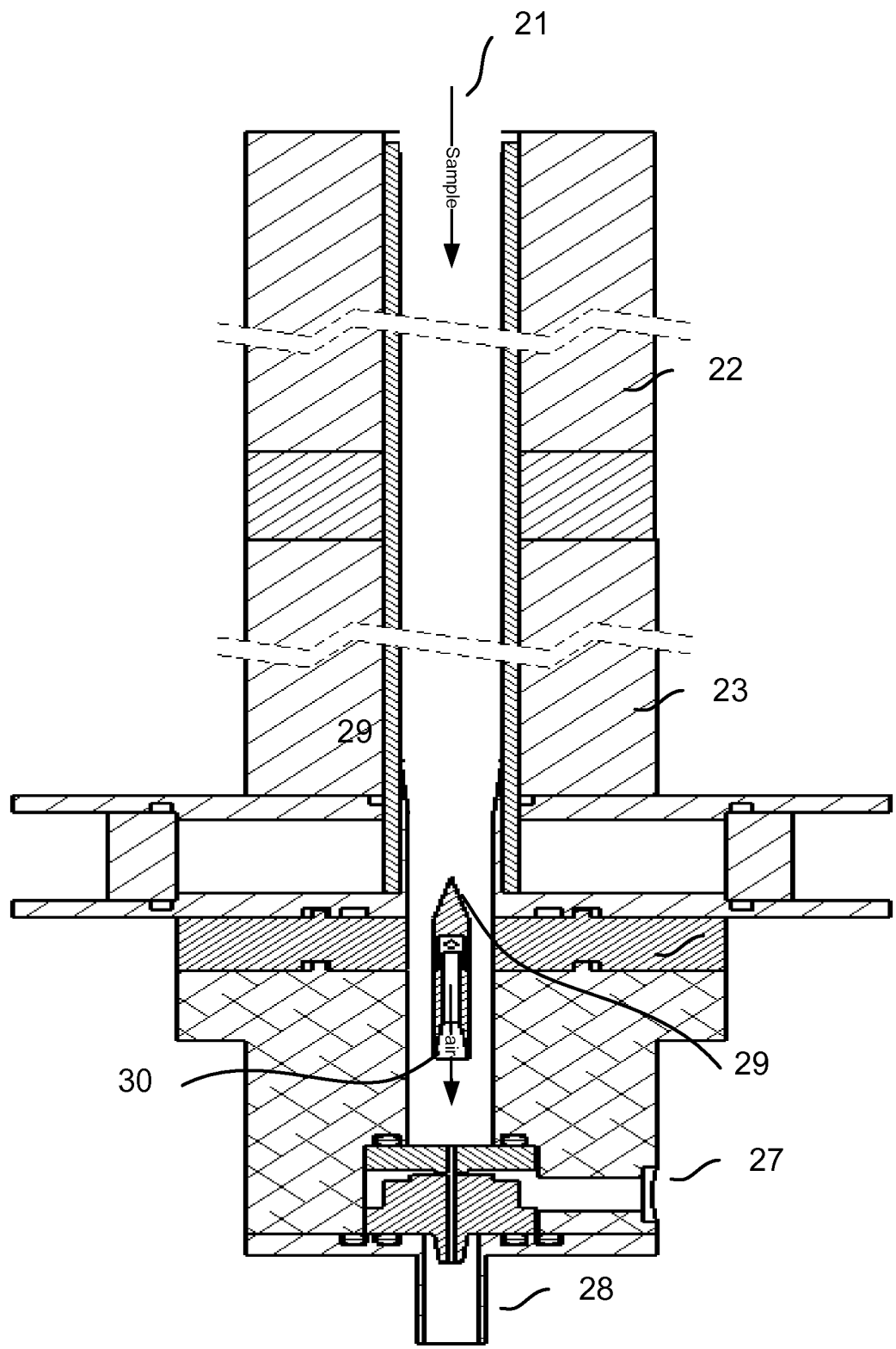
FIG. 7 shows an embodiment of the vapor-particle separation system wherein a clean core flow is introduced at the downstream end of the particle condensation system, immediately ahead of the nozzle concentrator.

FIG. 7 shows and example embodiment of the apparatus of the present technology employed as a vapor particle separator, where a clean air core flow is introduced immediately ahead of the acceleration nozzle by means of flow introduction nozzle 29 (support not shown). Port 29 is coupled to a controlled air supply which leads to the output of port 29. The particles enlarged by the condensation growth tube flow around this core flow introduction point, with the two flows joining at point 30. This core flow becomes the air that comprises the flow near the centerline of the nozzle, the majority of which becomes the particle transport flow that receives particles that by virtue of their inertial are thrown into the centerline flow.

The example embodiments have used cyclindrical geometries, but the basic principle applies to other geometries as well, including parallel plate configurations.

The effectiveness of the nozzle concentrator can vary based on its geometry and operating conditions. This has been evaluated through modeling and through experiment. As shown below, performance of the nozzle concentrator is dependent upon the sizing of the nozzle relative to the flow rate so as to focus particles of the size range of interest, and extraction of the side flow without deacceleration of that flow.

FIG. 8 shows the airflow stream lines for a simple, one-step system of FIG. 1, derived through numerical modeling. The modeled system is cylindrically symmetric with an entering an 8 mm internal diameter containment vessel, with a 0.86 mm diameter (d1) acceleration nozzle, a 0.1 mm sidewall extraction slit (e.g. 16) located a few nozzle diameters downstream from an entrance 14c (FIG. 4) of the acceleration nozzle. The edges of the slit and of the nozzle inlet have a 0.05 mm chamfer. Calculations are done for operation at a total volumetric flow rate of 1 L/min, with 80%-90% of this flow removed through the side flow extractor (e.g. 16) and the remaining 10%-20% of the flow continuing straight, and comprising the particle transport flow. Detail of the flow within the side flow extractor embodied as a slit is shown by the enlarged inset of FIG. 8. As shown in the inset, the slit is designed such that the magnitude of the velocity in the entrance of the slit is comparable to the mean velocity in the jet. Specifically, the width of the side flow extraction slit is less than 25% of the nozzle diameter. This provides a more stable flow that is less prone to mixing.

Figure 10:
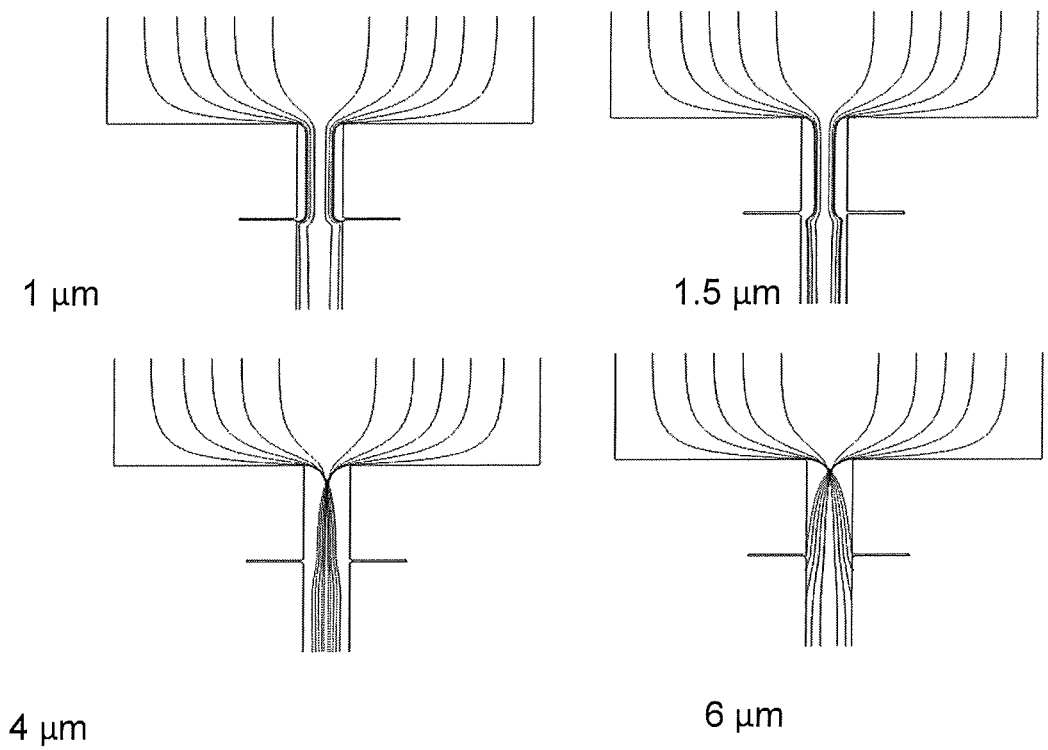
FIG. 10 presents calculated trajectories of 1 µm, 1.5 µm, 4 µm and 6 µm particles through for the geometry and flow conditions of FIG. 8, where the horizontal axis is expanded with respect to the vertical axis for easier viewing.

FIG. 9 shows the corresponding particle trajectories for a 3 µm particle seeded evenly across the entering flow. Details of the trajectories at the side flow extractor shown in the enlarged inset. As shown, the 3 µm particles are focused along the centerline and are not removed with the side flow. Calculated particle trajectories for this same geometry for particles with diameters of 1.0 µm, 1.5 µm 4 µm and 6 µm are shown in FIG. 10, where the horizontal scale has been expanded relative to the vertical scale for easier viewing. As illustrated, the concentration is effective over a window of particle sizes, with particles as small as 1.5 µm and as large as 4 µm being efficiently transported into the exiting particle transport flow. Smaller particles are not efficiently focused, and are partially lost with the extracted side flow, as illustrated by the trajectory for 1 µm particles. Larger particles cross the centerline of the flow, or 'over-focus'. While the trajectories for the 4 µm particles still remain within the particle transport flow, the larger 6 µm particles collide with the walls of the nozzle, or are lost through the side flow extractor.

Unlike virtual impactors used previously, the present flow separation is performed within the confines of the nozzle, without allowing the flow to discharge into a chamber. The current technology uses a nozzle concentrator with extraction structure within the nozzle concentrator to remove the majority of the air flow, leaving the particle-laden central flow to continue its trajectory through the nozzle to an output. Unlike previous virtual impactors, the extracted flow is not allowed slow, providing a stable separation of the central particle-enriched flow from the remaining majority flow.

Calculations of the type illustrated above were done at several air sampling rates, nozzle diameters, slit widths, and slit placement within the nozzle. The modeling shows that the nozzle concentrator performance depends on the ratio of the particle stopping distance to the nozzle diameter, a dimensionless quantity commonly called the Stokes number. The Stokes number equals $\rho C D_p^2 V/9\mu D_j$ where $\rho$ is the particle density, C is the Cunningham slip factor, $D_p$ is the particle diameter, $\mu$ is the carrier gas viscosity and $D_j$ is the diameter of the nozzle. With a single step the nozzle concentrator effectively concentrates particles with Stokes numbers in the range from 0.5 to 3.5. For an air flow of 1 L/min, this corresponds to a particle focusing window of 1.5 to 4 µm, as illustrated in FIG. 10.

Figure 11:
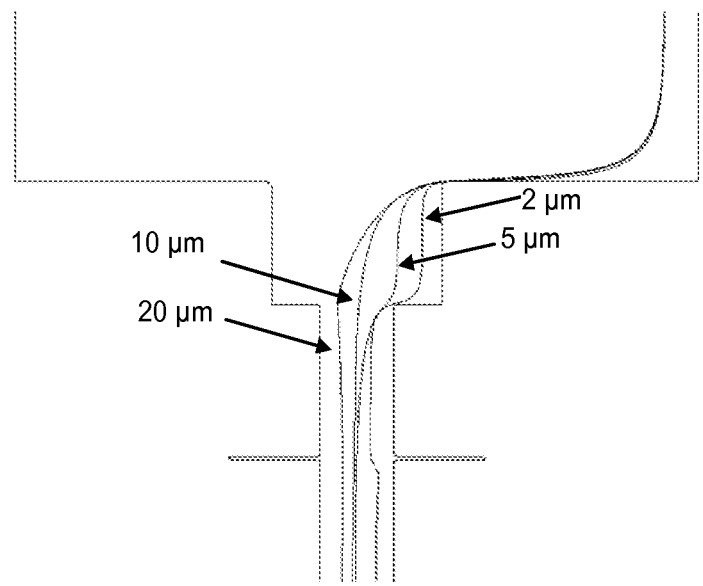
FIG. 11 presents calculated particle trajectories and transfer to central particle transport flow for 2 µm to 20 µm particles for a two-step nozzle concentrator. The horizontal axis is expanded with respect to the vertical axis for easier viewing.

By using multiple steps the effective window of particle concentration can be extended to larger particle sizes, but the lower size limit is not greatly affected. This is illustrated in FIG. 11, which shows modeled trajectories of several sizes of particles launched from near the outer edge of the flow when using a double-stepped nozzle concentrator of FIG. 5. In the example shown a 2 mm internal diameter orifice precedes the 0.86 mm acceleration nozzle, a 0.1 mm extraction slit located 5 mm downstream of the acceleration nozzle entrance, with a total flow of 1 L/min, and an extracted side flow of 0.8 L/min.

As can be seen from the modeling, operations of test devices occurred in a nominally laminar flow regime, with a Reynolds number for the flow is below 2200 for the nozzle, as well as for the entering flow. Apart from the Stokes number, the model calculations indicated that the performance is not very sensitive to the exact details of the parameters of the extraction structure. Numerical modeling of the system was done for a variety of proportions of slit widths, slit placements, and flow ratios. Results are similar to that shown for slits located between 1 and 6 nozzle diameters downstream from the nozzle entrance. Results for extraction flows ranging from 80% to 95% of the total inlet flow were almost identical to those shown here. Similar results were also found with a porous walled nozzle used as the extraction structure in place of the slit described above. Computations with wide slits did not converge, possibly indicative of unstable flow, which would degrade performance. In symmetrical nozzle concentrator designs, the extraction may be performed in a symmetric manner. For example, in a cyclindrical geometry, the extraction structure is either a radial slit or radially symmetric perforation in the walls of the nozzle.

Figure 12:
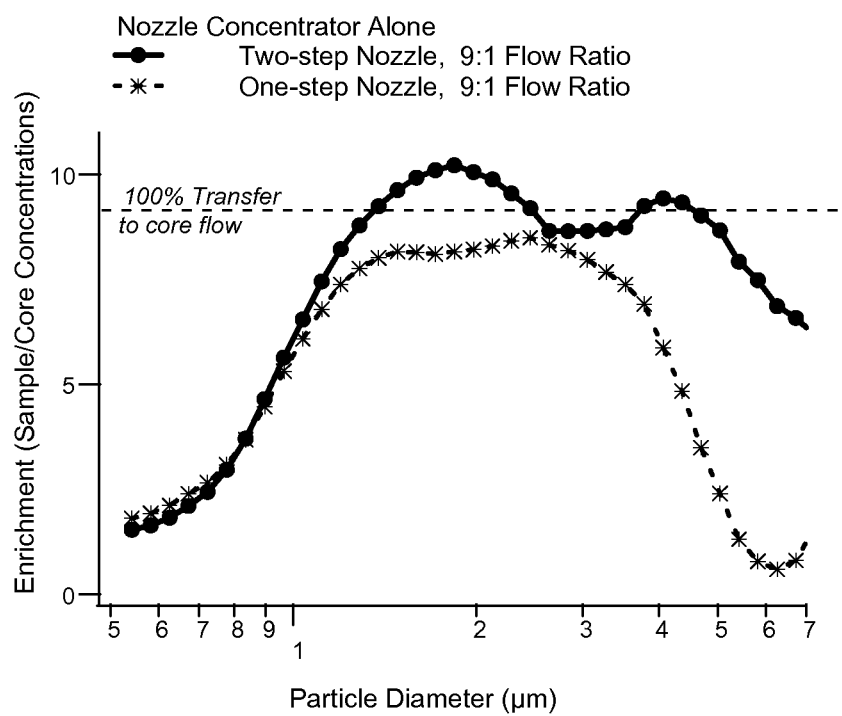
FIG. 12 is the measured enrichment in particle concentration in the central particle flow in tests with a liquid (sticky) aerosol using the nozzle concentrators of FIG. 4 and FIG. 5 when operated at 9:1 flow split. Total sample flow is 1. L/min, the extracted side-flow is 0.89 L/min and the central, particle transport flow is 0.11 L/min (measured at the inlet conditions).

Experimental measurements of the efficiency of the nozzle concentrator of the type shown in FIG. 4, are shown in FIG. 12. Critical dimensions are the same as for the model calculations of FIGS. 8-11. Air flow at 1 L/min (at atmospheric pressure) is introduced through a 8-mm ID tube. With the two-step nozzle the flow is passes through a 4-mm long, 2 mm ID orifice, and then through a 0.86 mm ID nozzle. The outer flow is extracted through a 0.1 mm gap located in the side wall of the nozzle, 4 mm downstream of the nozzle entrance. Model calculations also indicated that a porous wall could be used in place of the slit, but this was more difficult to construct, and so tests were done on the slit configuration of FIG. 4 and FIG. 5.

Tests were done with a polydisperse, liquid aerosol generated by nebulization. An Aerodynamic Particle Sizer (available commercially from TSI Inc.) was used to measure the size-dependent concentration of the aerosol in the upstream sample flow, and in the downstream particle transport flow. The enrichment, defined as the ratio of the particle concentration in the downstream particle transport flow to the particle concentration in the upstream sample flow, is plotted in FIG. 12. Data are shown for both the single-step and two-step nozzle configurations. These experiments were conducted with a sample:particle transport flow ratio of 9, meaning that the exiting particle-enriched flow is $\frac{1}{9}^{th}$ of the total sample flow. Thus the largest possible enrichment, corresponding to 100% transmission of particles from the sample flow into the particle transport flow is 9, as indicated by the dashed line. Note that for small particles the behavior is similar, with 50% transmission at 1 µm, but the two-step nozzle shows improved enrichment for larger particles (4-7 µm), as predicted by the modeling.

These tests were conducted using a liquid aerosol which will adhere to the walls of the system upon impaction, and thus the enrichment factors measured are not confounded by rebound from the particle walls. These results show that agreement with the model results in the range from 1-6 µm, with the enhancement of the particle concentration in the particle transport flow nearly equal to the product of the flow split and the upstream concentration. This means that within the window of transmitted particle sizes, nearly 100% of the particles from the sample flow find their way to the 11% of the particle transport flow, providing close to a 9-fold enrichment in particle concentration.

The present technology may be implemented with a water condensation growth tube for ultrafine particle concentration.

The concentration of ultrafine particles, which are too small to be focused at atmospheric pressures by the nozzle concentrator of FIG. 4, is facilitated by first enlarging the ultrafine particles by water condensation. In the present implementation of this technology this is done using the differentially diffusive, laminar flow water condensation device based on the principles of U.S. Pat. No. 6,712,881. This device, used as the containment vessel, is commonly called a "growth tube" and consists of a single tube with two sections of wetted walls separated by a thermal break. The first section is cooled, and the second section is warmed, and the flow is laminar throughout. In the second half the flow becomes supersaturated as a result of vapor transport into the cooler flow from the warm, wetted walls. In this supersaturated region particles above a critical size will grow by condensation, including those that are non-hygroscopic. Creation of a region of vapor supersaturation aids the activation of condensational growth on small particles because the energy associated with the droplet surface elevates the equilibrium vapor pressure over a droplet as compared to a flat surface of the same chemical composition.

Important to the application of condensational growth to the nozzle concentrator is that the size distribution of the droplets formed from the condensation process is nearly monodisperse. This is to say that once activated, the size of the droplets formed is essentially independent of the size of the particle that served as the nucleus for the droplet growth.

Figure 13:
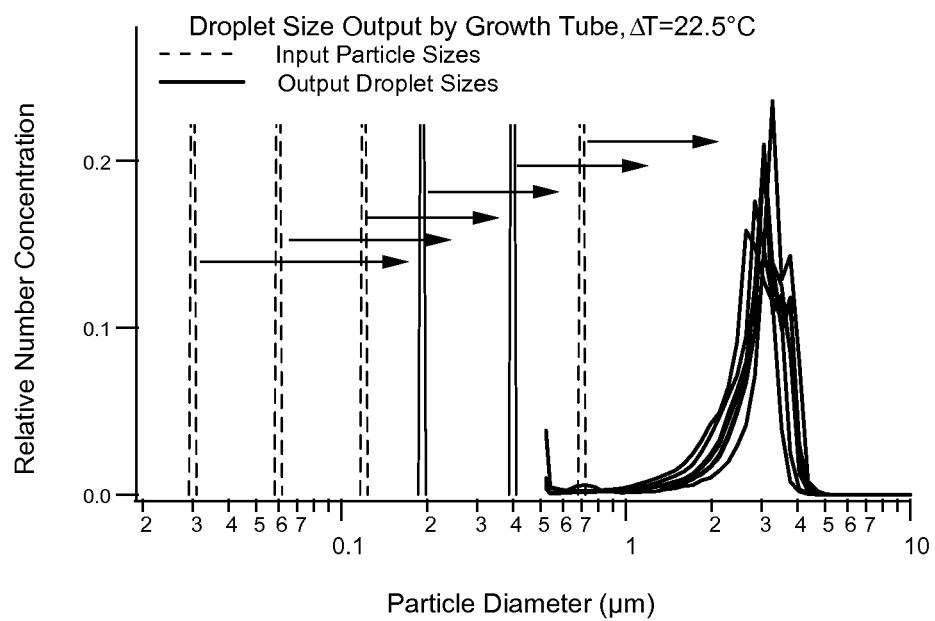
FIG. 13 is the measured droplet size distribution at the exit of the standard (1 L/min) laminar-flow, water condensation growth tube for five different input particle sizes, ranging from 30 nm to 700 nm.

FIG. 13 shows measurements of the output droplet size for a containment vessel comprising a growth tube used in the implementation of this technology. It consists of a single, 230 mm long, 9.5 mm ID wet walled tube through which air flows in a mostly laminar manner at 1 L/min. The first portion of the tube is cooled with respect to the second portion. For the data shown in FIG. 13 the tube walls at the entrance region are cooled to 2° C., while those in the second portion of the tube are heated to 22° C. Monodisperse aerosols obtained by electrical mobility selection using a differential mobility analyzer were introduced into the growth tube, and the output droplet size distribution was measured using an Aerodynamic Particle Sizer (Model APS 3321, TSI, Inc.). Input aerosols with diameters varying from 30 nm to 200 nm produces uniformly sized droplets with a diameter near 3 µm. The efficiency of droplet formation was measured as 98+−5%.

As can be seen by comparing FIG. 13 to FIG. 12, the droplet size exiting the growth tube fits exactly within the window of focused particle sizes from our nozzle concentrator system. Therefore, we combine these two technologies to provide concentration of ultrafine particles. Note further that unlike the prior methodologies, the temperature to which the particles are exposed is not extreme, indeed the final temperature is simply room temperature.

Figure 14:
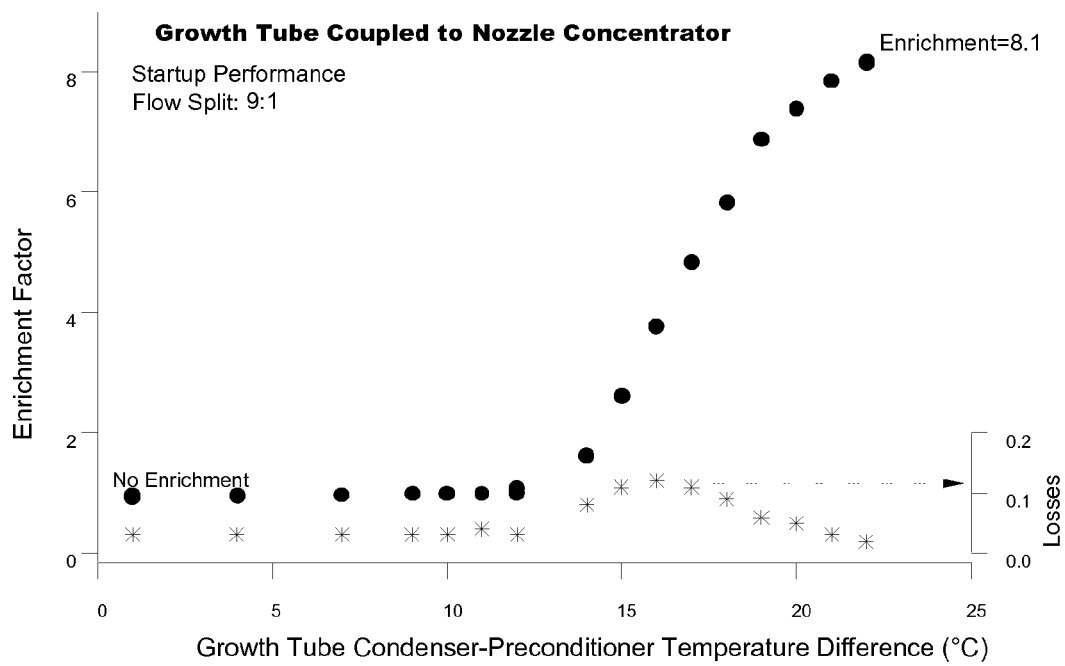
FIG. 14 is the measured enrichment and loss of 100 nm particles with water condensation growth tube coupled to the nozzle concentrator during startup, with the growth tube off, and then as the preconditioner is cooled with respect to the condenser.
Figure 15:
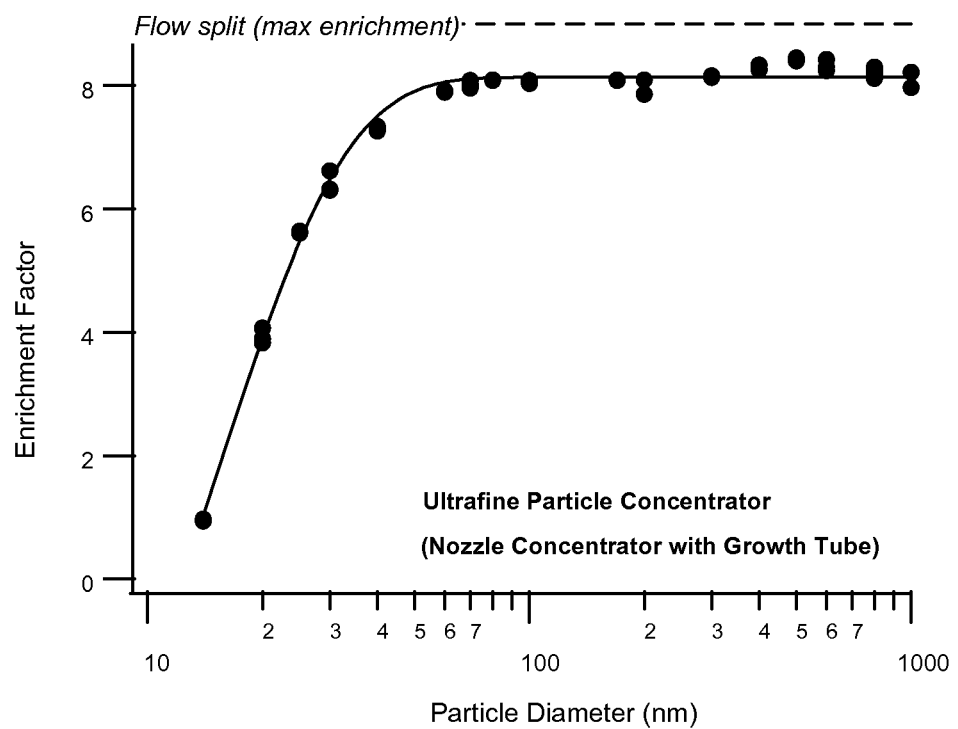
FIG. 15 shows the measured enrichment of particle concentration in the central, particle transport flow as a function of particle size.
Figure 16:
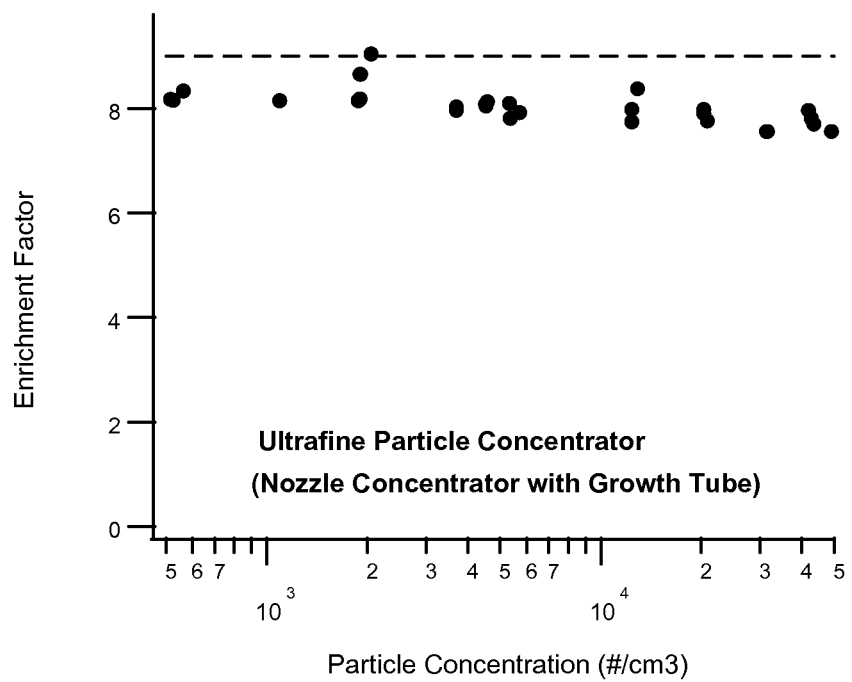
FIG. 16 shows the measured enrichment as a function of input particle number concentration for a fixed particle diameter of 100 nm.

FIGS. 14-16 present results from laboratory experiments conducted with the geometry of FIG. 6, where the 1 L/min growth tube was coupled to the two-step concentrator of FIG. 5. Experiments were done using mono-disperse, non-hygroscopic particles composed of ammonium fluorescein. Particle concentrations were measured in all three flows, the upstream aerosol flow, the downstream particle transport flow and in the downstream side flow. The growth tube operated with the preconditioner at 2° C. and the condenser, or growth section, at room temperature of 24° C. At this relatively small temperature differential, approximately 90% of the particles are activated to form droplets, as confirmed by direct measurement of the droplet diameter with an Aerodynamic Particle Sizer. Those not activated are likely the particles near the wall of the growth tube, where the presence of the wall limits supersaturation of the water vapor.

FIG. 14 shows the efficiency at startup, when the growth tube is off, and then as the growth tube is turned on. Shown is the efficiency for transfer of 100 nm particles from the 1 L/min entering flow were transferred into the 0.11 L/min particle transport flow as a function of the temperature difference between the condenser and preconditioner regions of the growth tube. When this temperature difference is zero, the growth tube is "off", and there is no supersaturation, no activation and particle growth. Under these conditions the penetration of particles from the sample air flow to the particle transport flow simply equals the flow split, the ratio of the particle concentration in the particle transport flow to that in the sampled air flow is 1. The temperature difference is increased by lowering the temperature of the preconditioner, while maintaining a fixed temperature of 24° C. for the condenser. At a critical temperature difference of around 15° C., the droplets are large enough for some of them to be focused, and the enrichment factor defined as the particle transport-sample flow concentration ratio, begins to increase. At a temperature difference of 22° C. the essentially all of the 100 nm particles are transmitted to the particle transport flow. Also shown on FIG. 14 are the losses, measured by comparing the sum of particles in the side and particle transport flows to the sample flow. These losses reach 10% at the transition region, when only some of the droplets are large enough to be focused. But the losses are less than 3% at when the final operating temperature difference of 22° C. is achieved.

FIG. 15 presents the size-dependent particle concentration enrichment measured for monodisperse, nonhygroscopic aerosol once the growth tube reached its final operating temperature, here set to 2° C. for the preconditioner and 24° C. for the condenser. Note that all particles above 60 nm are focused with 90% efficiency (enrichment factor of 8.1 compared to a theoretical maximum of 9.0). The efficiency drops to 50% at around 20 nm, (enrichment of 4.5 When operation at a somewhat larger temperature difference occurs, for example by increasing the condenser temperature to 37° C., enrichment of particles as small as 7 nm can be achieved.

FIG. 16 shows the enrichment as a function of the particle number concentration for 100 nm particles. These tests were done because experiments and modeling both indicate that under some system geometries the condensational heat release within the growth tube can reduce the final droplet size. Consistent performance across all particle concentrations was found.

These results demonstrate the ability to focus and concentrate 90% of the aerosol into a particle transport air flow, independent of the initial particle size or concentration. The corresponding enrichment factor is 8.1, out of a theoretical maximum of 9.0.

The system may also be used as a Vapor Particle Separator. Separate collection of vapor and particle phases of semi-volatile constituents is a formidable challenge. Mostly commonly vapor denuder systems are used in conjunction with absorbing collection substrates, but denuder systems, including those routinely used for integrated sampling, are subject to the inefficient collection of the vapor constituents.

Figure 17:
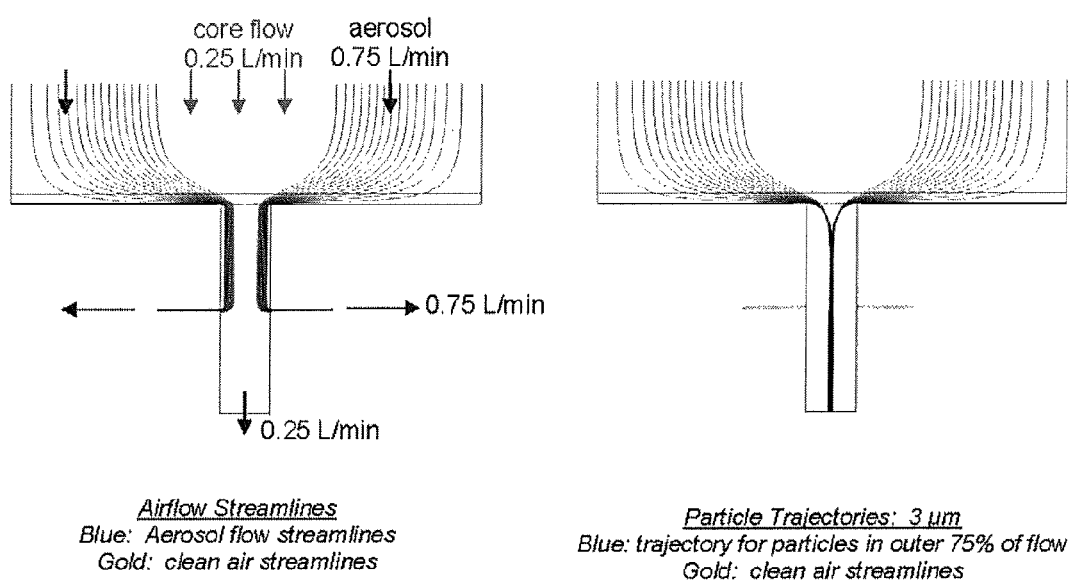
FIG. 17 shows implementation of the technology as a particle-vapor separator, with a clean air core flow introduced upstream of the nozzle concentrator.

With the current technology, ultrafine and submicrometer particulate matter are grown through water condensation to uniformly sized, supermicrometer droplets, and then to immediately propelled into a clean, dry air flow. FIG. 17 shows model results when a clean air flow is introduced in the center of the sample flow, just upstream of the acceleration nozzle. By maintaining a laminar flow, the core air flow that remains after the extraction of the side-flow is derived from this central sample flow. Thus this becomes the downstream core air flow. The particles that have been enlarged through condensational growth are focused at the entrance of the acceleration nozzle, and thrown into this core flow. By using a clean, dry-air core, the particles will lose their water, returning to their initial size. By correctly sizing the system, such that the droplet growth occurs immediately ahead of the acceleration nozzle, the time that the droplets spend in the original aerosol flow can be very short, of the order of 100 ms, thereby minimizing the uptake of soluble vapors that could affect the particle chemistry. Experimental evaluation of this approach shows that the ideal separation between the core flow and the sampled air is achieved with a single-step acceleration nozzle, where the core flow of around 15% of the total flow entering the acceleration nozzle, and the particle transport flow is 10% of this total (with corresponding air sample flows of 85% and 90% respectively.)

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A particle concentration apparatus comprising:
a particle laden flow containment vessel, the vessel having a particle laden flow entering at one end of the flow containment vessel;
a nozzle concentrator having an inlet provided at a second end of the flow containment vessel, the nozzle concentrator including an acceleration nozzle having at least one interior wall defining a passage having a width, the passage bisected by a centerline between the inlet and an outlet such that the particle laden flow from the flow containment vessel is accelerated into the inlet of the passage and along the centerline, and a flow extraction structure positioned in the interior wall between the inlet and the outlet and having a smaller width than the passage.

2. The apparatus of claim 1 wherein the interior wall has circular cross-section and a nozzle diameter selected such that a dimensionless quantity comprising a ratio of the particle stopping distance to the nozzle diameter of $\rho C D_p^2 V / 9 \mu D_j$ is between 0.5 and 3.5 for particle diameters that are to be focused.

3. The apparatus of claim 1 wherein extraction structure comprises a radial extraction outlet including a symmetric perforation in the at least one interior wall of the nozzle.

4. The apparatus of claim 3 wherein the symmetric perforation is a radial slit.

5. The apparatus of claim 4 wherein the interior wall has circular cross-section and a diameter, and the radial slit is located at a distance which is in a range of approximately 1 to 10 times the diameter downstream from an entrance point of the nozzle in the containment vessel.

6. The apparatus of claim 4 wherein the radial slit has a width and the width of the slit is chosen so that that a mean flow velocity in the slit is comparable to a mean flow velocity in the nozzle.

7. The apparatus of claim 4 wherein the radial slit has a width and the width of the slit is chosen to be less than 25% of a nozzle diameter.

8. The apparatus of claim 1 wherein the extraction structure removes an extracted flow, and the extracted flow is 70% to 95% of the total flow entering the nozzle from the containment vessel.

9. The apparatus of claim 1 wherein the extraction structure removes an extracted flow, and the extracted flow is 80% to 95% of a total flow entering the nozzle from the containment vessel.

10. The apparatus of claim 1 wherein a Reynolds number of a flow in the nozzle is below 2200.

11. The apparatus of claim 1 wherein the apparatus further includes a flow controller for the particle laden flow having a flow rate within the containment vessel, and wherein a nozzle diameter and a flow rate are selected to give a Stokes number between 0.5 and 3.5 for the particle size range to be focused.

12. The apparatus of claim 1 wherein the containment vessel includes one of a water based particle condensation system and/or a particle-free laminar flow introduced into the containment vessel.

13. The apparatus of claim 1 wherein the nozzle concentrator further includes an input focusing portion having interior walls, the interior walls having a diameter greater than the acceleration nozzle.

14. The apparatus of claim 1 wherein the second end of the vessel includes at least one bottom wall having a surface perpendicular to the centerline, and the interior wall is perpendicular to the bottom wall.

15. The apparatus of claim 14 wherein the interior wall meets the surface to form an edge.

16. A particle concentration method, comprising:
introducing a particle laden flow into a containment vessel at a first end of the vessel;
accelerating the particle laden flow at a second end of the containment vessel using a nozzle having an input and an output and an interior wall defining a width between the input and output with a centerline bisecting the width of the nozzle;
simultaneously extracting a portion of the flow passing along the centerline of the nozzle and adjacent to the interior walls using an extraction structure in the interior wall, the extraction structure having a width smaller than the width of the nozzle; and
transporting non-extracted flow as a particle enriched flow to an output of the nozzle along the centerline.

17. The method of claim 16 further including enlarging particles in the particle laden flow prior to accelerating through condensational enlargement.

18. The method of claim 17 wherein condensational enlargement is achieved through a laminar flow water condensation device.

19. The method of claim 16 further including introducing a separate core flow immediately upstream of the nozzle concentrator into which the particles are propelled.

20. The method of claim 16 wherein the step of simultaneously extracting comprises providing a radial slit having a width chosen so that that a mean flow velocity in the slit is comparable to a mean flow velocity in the nozzle.

21. The method of claim 16 wherein the step of simultaneously extracting comprises providing a section of porous wall in the nozzle.

22. The method of claim 16 wherein the step of simultaneously extracting comprises removing an extracted flow, and the extracted flow is 70% to 95% of a total flow entering the nozzle from the containment vessel.

23. The method of claim 16 wherein the interior wall has circular cross-section and a diameter selected such that a dimensionless quantity comprising a ratio of the particle stopping distance to the nozzle diameter of $\rho C D_p^2 V / 9 \mu D_j$ is between 0.5and 3.5 for particle diameters that are to be focused.

* * * * *

UNITED STATES PATENT AND TRADEMARK OFFICE
CERTIFICATE OF CORRECTION

PATENT NO. : 8,459,572 B2  
APPLICATION NO. : 12/910705  
DATED : June 11, 2013  
INVENTOR(S) : Hering et al.

Page 1 of 1

It is certified that error appears in the above-identified patent and that said Letters Patent is hereby corrected as shown below:

In the Claims

Col. 10, line 15: After "10" and before "times", insert a space in between.

Col. 10, line 18: After "so" and before "that" delete "that".

Col. 11, line 12: After "so" and before "that" delete "that".

Signed and Sealed this
Tenth Day of December, 2013

Margaret A. Focarino
*Commissioner for Patents of the United States Patent and Trademark Office*